United States Patent [19]
Tyner et al.

[11] Patent Number: 5,752,813
[45] Date of Patent: May 19, 1998

[54] KEYED CASSETTE FOR DISPENSING PUMP

[75] Inventors: Cliff Tyner, Grass Valley; Lawrence J. Dahlhauser, San Ramon, both of Calif.; Steven Gorn, Boca Raton, Fla.; Laurence R. Nicholson, Nevada City, Calif.; Stuart Meadow, Boca Raton, Fla.; Jeffrey H. Feigenbaum, Brooklyn, N.Y.

[73] Assignee: A.Z.E. Medical Inc., Brooklyn, N.Y.

[21] Appl. No.: 735,900

[22] Filed: Oct. 23, 1996

[51] Int. Cl.⁶ .................................... F04B 43/00
[52] U.S. Cl. ............. 417/477.2; 417/412; 128/DIG. 12
[58] Field of Search ................... 417/477.2, 412; 604/65, 66, 67; 128/DIG. 12

[56] References Cited

U.S. PATENT DOCUMENTS

| | | | |
|---|---|---|---|
| D. 264,134 | 4/1982 | Xanthopoulos | 417/477.2 |
| 4,605,396 | 8/1986 | Tseo et al. | 123/DIG. 12 |
| 4,735,558 | 4/1988 | Kienholz et al. | 417/477.2 |
| 4,784,577 | 11/1988 | Ritson et al. | 604/65 |
| 4,790,816 | 12/1988 | Sundblom et al. | 604/67 |
| 5,364,342 | 11/1994 | Beuchat et al. | 123/DIG. 12 |

*Primary Examiner*—Timothy Thorpe
*Assistant Examiner*—Cheryl J. Tyler
*Attorney, Agent, or Firm*—Israel Nissenbaum

[57] ABSTRACT

A method for the enhanced accuracy in dispensing from a fluid roller dispensing pump, wherein a keyed one way insertable cassette with pump compressible tubing is utilized with the fluid dispensing pump. The cassette holds and maintains a compressible plastic tube adjacent a roller pump, whereby the rollers of the pump compress the tubing to draw and accurately dispense predetermined exact amounts of liquids into vials, hypodermics and the like for accurate medical and/or laboratory use, and wherein slightly improper placement still provides dispensing but with not always detectable inaccuracies. The cassette is provided with positive proper position indicator elements to ensure both proper orientation and complete locking engagement to ensure accurate pumping and dispensing. In a preferred embodiment the pump embodies current use sensors which determine if the cassette, which causes the pump to use more current, is present. A keyed one-way cassette fitting prevents improper placement.

3 Claims, 5 Drawing Sheets

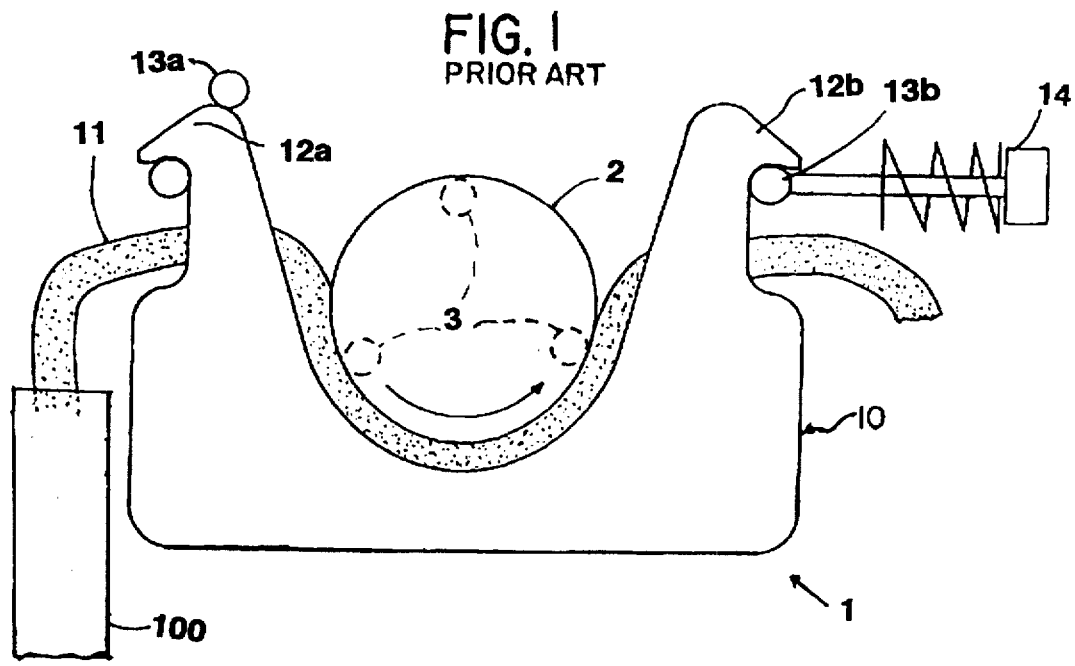
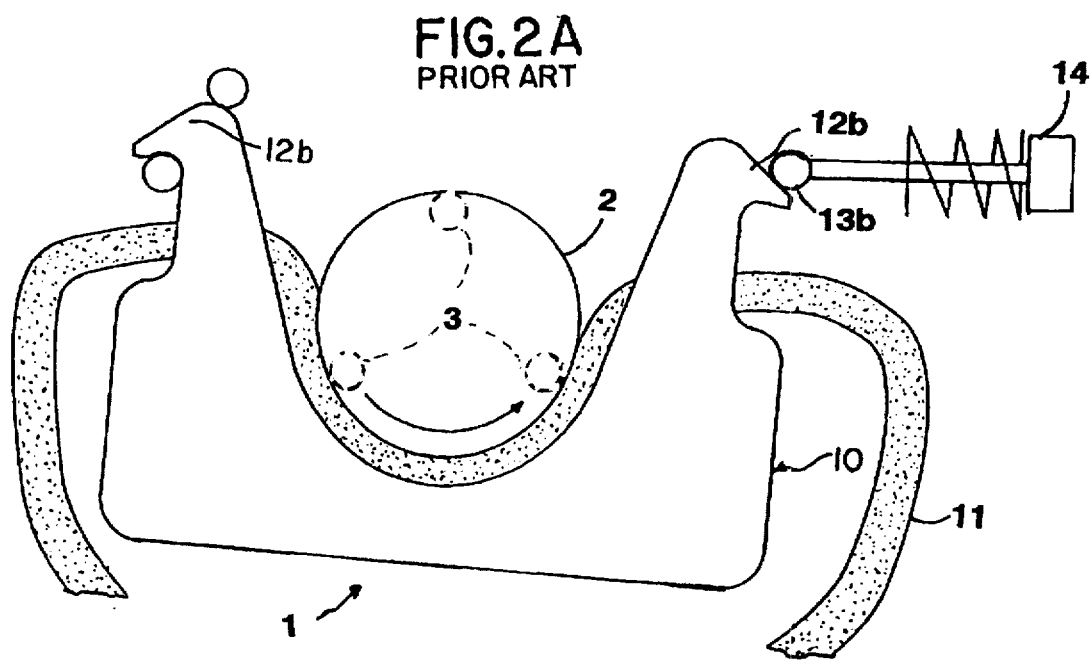

5,752,813

KEYED CASSETTE FOR DISPENSING PUMP

FIELD OF THE INVENTION

This invention relates to roller type peristaltic pumps for dispensing fluids by means of tubing compression and particularly to cassettes which hold the tubing in position for such pumping.

BACKGROUND OF THE INVENTION

Roller type peristaltic pumps are comprised of a rotating element having multiple spaced free-rotating roller elements positioned thereon, such as described in U.S. Pat. Nos. 4,976,590 and 5,024,347. This type of pump is operable by positioning a compressible dispensing tube adjacent the roller elements such that the rollers successively compress and release the compressible tubing to pulse pump liquids therethrough. Liquid pumping is accurately effected with the pumping strokes providing determinable amounts of pumped liquid, based on pump turns. Reversal of the rotation results in reversal of the fluid flow.

It is important that the tubing be properly and fixedly positioned for accuracy in pumping and proper operation. Accordingly the tubing is normally contained within a supporting cartridge which is used to position and lock the tubing directly against the pump rollers during a metered filling operation from a dispensing container (one end of the tubing) into a vial or hypodermic (the other end of the tubing). The cartridges are usually symmetrical whereby the cartridge can be reversed (with a reversal of tubing connections).

However, several problems exist with such system, with some not being readily detectable. The cartridges are provided with dual latching engagement means to ensure that the cartridge is fixed into position. However, it has been discovered that the pumping procedure can be effected, albeit improperly, with full engagement of only one of the latching means, and only partial engagement of the other, whereby the tubing is juxtaposed against the pump rollers but without a full and proper engagement latching of the pump rollers against the tubing. Since the partial engagement does, in fact, permit nearly complete pumping, there is no discernible indication of the improper engagement and possible inaccuracies in the measured dispensing. In addition, if the cassette is not properly loaded, the solution is likely to free flow or back flow through the tubing set.

Furthermore, if the cartridge is latched to the pump after the tubing has been connected, and particularly if the tubing is lengthy, there is a real possibility of the cassette being inserted with a latching but a reverse orientation, which is not readily detected, wherein the flow reverses in the tubing set, which may result in the user connecting the supply bottle to the discharge side and the empty device to the supply side.

SUMMARY OF THE INVENTION

It is therefore an object of the present invention to provide means to permit operable cartridge operation and fluid flow with a roller type peristaltic pump, only with a single orientation of the cartridge, relative to the pump, and a full engagement therewith.

These and other objects, features and advantages of the present invention will become more evident from the following discussion and drawings in which:

SHORT DESCRIPTION OF THE DRAWINGS

FIG. 1 is a schematic view of the interior of a prior art roller type peristaltic pump properly engaged with a cassette for the pumping of a liquid from a source to a vial, with solution flow being indicated by the arrows;

FIG. 2a is the schematic view of FIG. 1 but with an incomplete latching.

Figure 5:
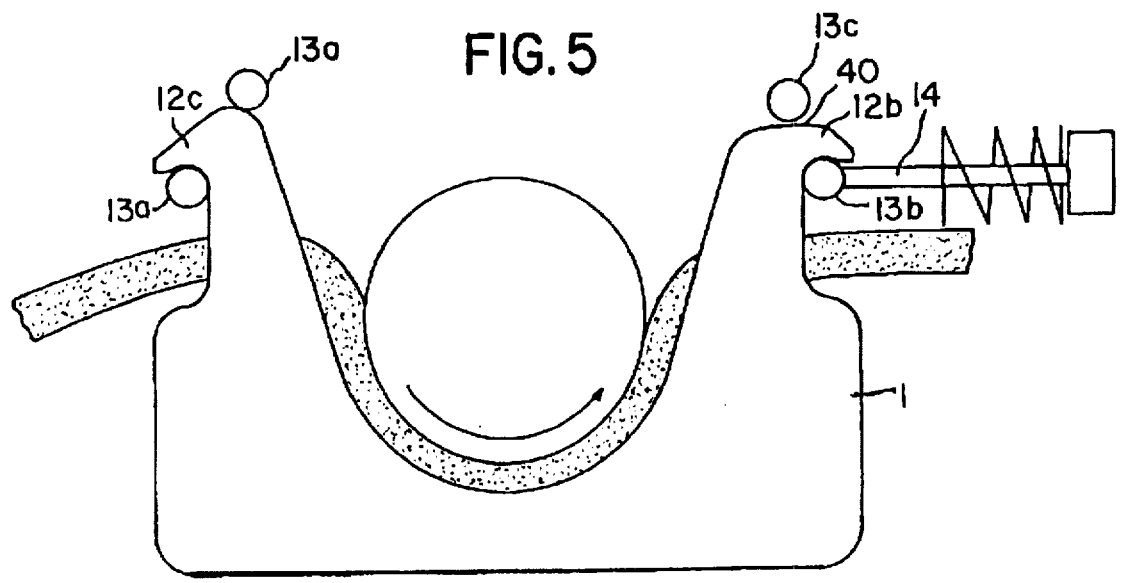
Figure 6:
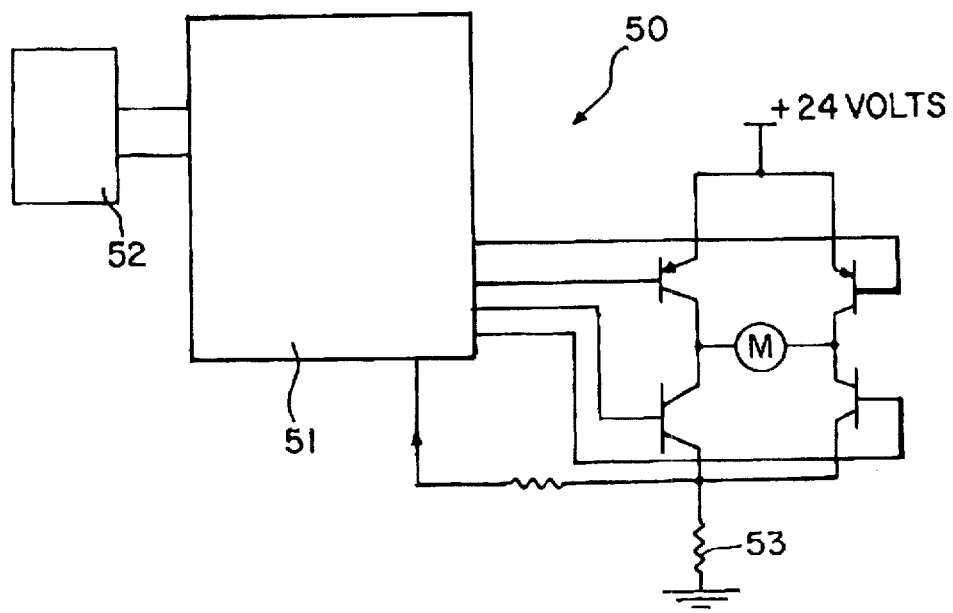

FIG. 5 schematically depicts a current sensing and notched cassette embodiment; and FIG. 6 is a schematic of the electronics utilized in detection of cassette presence in the embodiment of FIG. 5.

DETAILED DESCRIPTION OF THE INVENTION

Generally the present invention comprises a rotary peristaltic pump with roller pumping members and a tubing cassette, adapted to be affixed to the rotary pump to juxtapose the tubing and the roller pumping members to effect measured pumping of a solution from a dispensing container source to a vial or hypodermic. In accordance with the present invention, one of the pump and the cassette is provided with sensing means and the other of the pump and cassette is correspondingly provided with pump activation means (i.e., causing activation via the sensor). Since the pump is connected to an electrical supply, it is preferred that the sensing means for control of the pumping system (electrically operable) be directly positioned on the pump.

With a non-symmetrically positioned sensor, there is only one orientation for the cassette. Accordingly, only when the cassette is properly oriented and fully locked in position, is the sensor activated by the pump activation means, whereby solution dispensing, via the pump, is activated or is available for actuation.

Examples of sensors include magnetic, optical and mechanical means to create an interlock. Thus, an effective sensor comprises a reed switch or a Hall effect sensor, coupled with an actuating magnet, wherein there is an embedded magnet within the cassette and a magnetic-sensitive switch within the pump housing. Juxtaposition, of the elements, with a proper cassette engagement, triggers the sensor and activates the pump operation.

An optical sensor, utilized in accordance with the present invention, comprises an interrupter flag or a reflective sensor, with the reflective optical sensor being mounted on the surface of the pump housing to "see" a reflective piece adhered to the cassette at the proper location. Care must be taken with this type of sensor to avoid inaccuracies caused by solution spills on the sensor elements and which may obscure or warp "visibility".

A mechanical contact switch can similarly be utilized to ensure proper orientation and position. In such embodiment a small finger protrudes from the cassette, preferably within an indentation to avoid possible breakage. The finger activates a sealed mechanical switch which protrudes through the pump housing.

Since locking and release of the cassette is usually at the right hand side and this area is where the incomplete latching is most likely to occur, it is preferred that the sensor and actuating elements be located in such area.

To ensure that the cassette and pump cannot be "hot wired" with bypass of the system, software used in monitoring and running the pump includes a self determination check to see if the sensor has been tampered with or removed.

Because of the wet environment and in view of factors of space and cost considerations, a more preferred system embodiment involves a combination of motor current sensing and interlock pins, similar to the mechanical finger as described. With an interlock switch, a small switch is opened when the cassette is installed. Unless the cassette is fully installed, the pump will not operate. To this effect, the cassette embodies a small bump at the tip of the engaging element which bump is visible through the clear plexiglass of the pump. The switch in the pump must be protected against water spray and is encased and mounted between the pump casing and the plexiglass casing.

In the more preferred combination of current sensing and locating pins embodiment, the pump motor current is utilized to sense the presence of a cassette. An internal memory in the pump is adapted to remember the range of current when the cassette is operatively installed. If the current drops below this range, the pump assumes that no cassette is present. In order to sense cassette presence, the motor is turned on and the voltage across a current sensing resistor is proportional to the motor current. With no cassette, the sensing voltage is lower than with a cassette. Software logic is used to determine typical loaded current values and if the sensing voltage falls below this level by a certain fixed voltage or percentage, the pump motor is adapted to immediately turn off with the job being terminated.

To insure that the cassette is installed properly and in the right direction, a locating pin is installed in the pump housing to mate with a notch at the upper tip of the right side of the cassette. The opposite side tip does not have the notch. If the right side did not have the notch, the cassette would not install all the way and the software which drives the pump would sense that no cassette is present. If the left hand side were made with a notch, as might occur if it were desired to bypass the system by providing both sides with notches, the cassette would fit loosely with resultant unacceptable accuracy, especially for devices like balloon pumps. This embodiment is preferred since it requires no additions to the cassette or the pump and it does not embody any parts that might fail when exposed to liquids.

DETAILED DESCRIPTION OF THE DRAWINGS AND THE PREFERRED EMBODIMENTS

Figure 2B:
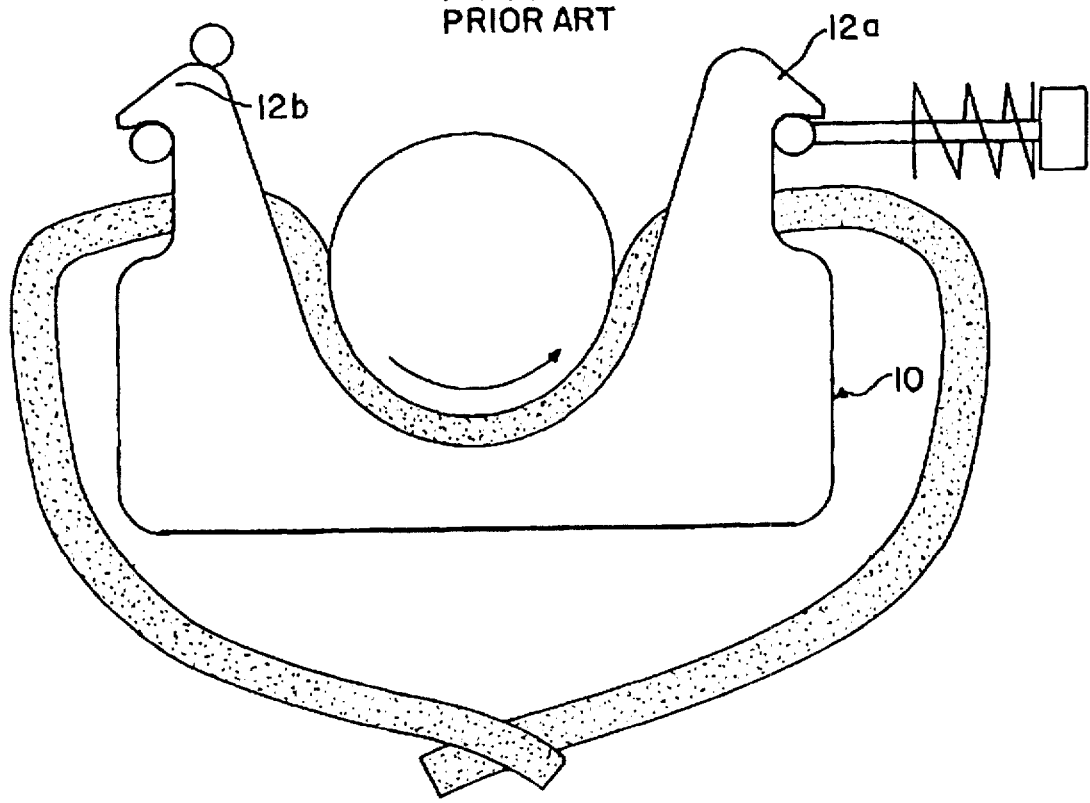
FIG. 2b is the schematic view of FIG. 1 but with reversed cassette insertion.

With specific reference to the drawings, in FIG. 1, a peristaltic pump 1, with a rotating pump member 2, comprises a series of rollers 3 which rotate against plastic tubing 11, through which a solution is being transported in the direction as indicated by the arrows from container 100. The tubing is retained within cassette 10, which provides and maintains the requisite juxtaposition between the rollers 3 and the tubing 11 to accurately effect the pumping. The cassette 10 is originally installed on the pump by engagement of latching elements 12a and 12b of the cassette with locating pins 13a and 13b on the pump respectively. Latching element 12a is initially fitted between pins 13a and then latching element 12b is fitted to movable pin 13b (held in place by spring loaded latch 14) to effect the locking placement (latch 14 is pulled, to release pin 13b, and removal of the cassette from the pump). However, as shown in FIG. 2a, it is possible to partially hold the cassette with pin 13b but without a complete engagement, with concomitant partial release of pumping pressure between rollers 3 and the tubing 11. In addition, as shown in FIG. 2b, reversal of the cassette, which is symmetrically constructed, reverses the direction of the tubing and the direction of fluid flow. If the tubes are long, such reversal might not be noticed.

Figure 4A:
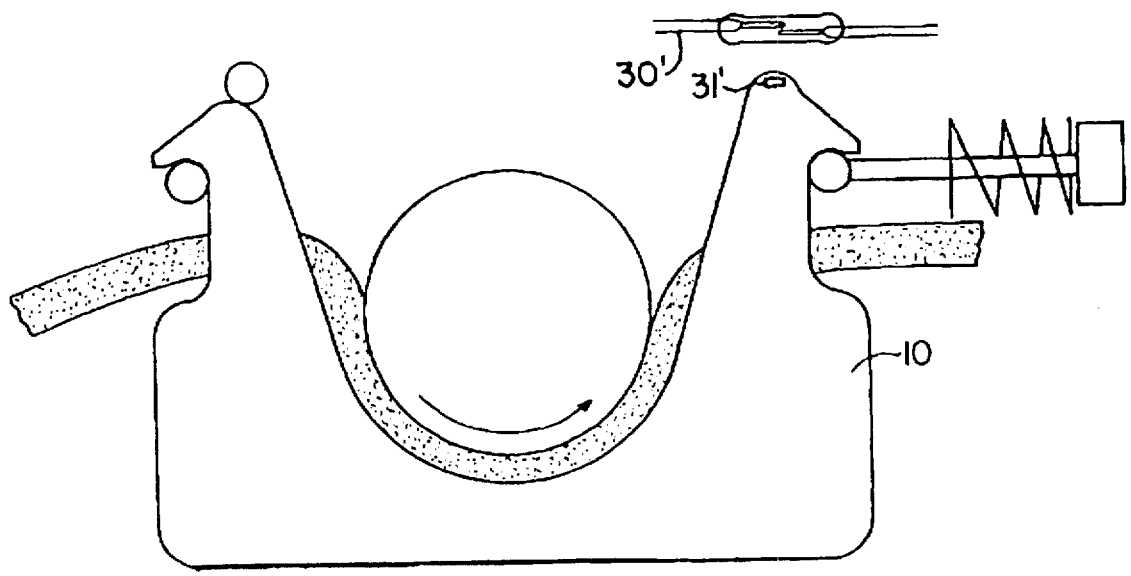
FIGS. 4a–c schematically depict operative arrangements of magnetic, optical and mechanical types of sensor and actuation embodiments respectively of the present invention.
Figure 3:
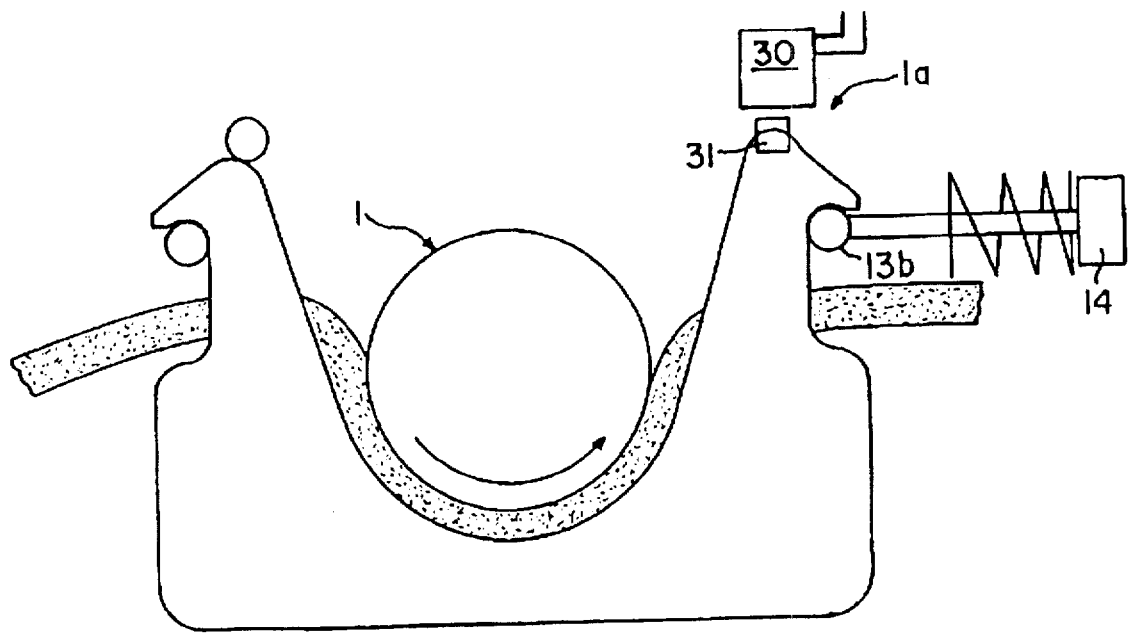
FIG. 3 is the cassette of the present invention shown with proper orientation and complete latching with verification means.
Figure 4B:
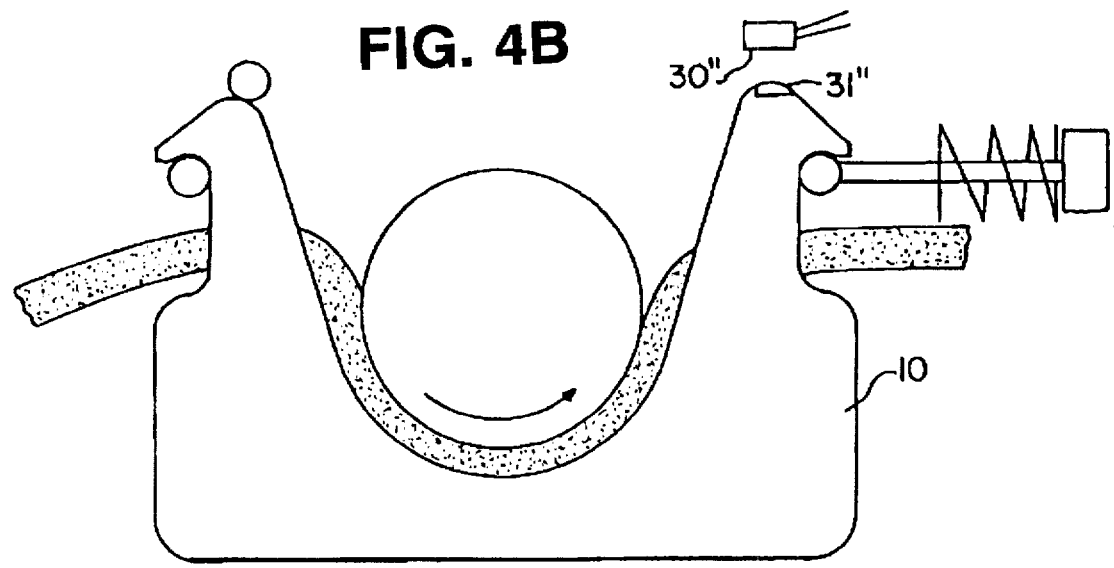
Figure 4C:
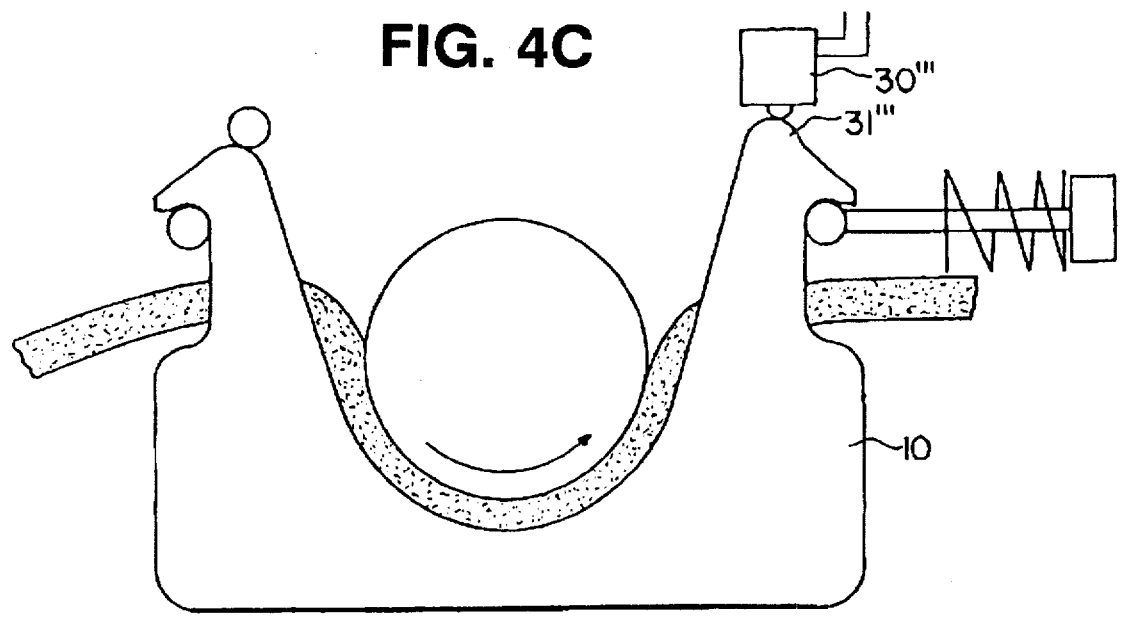

In accordance with the present invention, as shown in FIG. 3, the pump 1, in the area 1a, adjacent the movable pin 13b, is provided with a sensor 30 and cassette 10 is provided with a sensor triggering element 31 which operatively triggers sensor 30 to permit pumping, by opening a safety interlock not shown in the pump controls. Element 31 triggers sensor 30 only when they are aligned, with full seating of the cassette in a proper orientation. The sensor 30 and element 31 are asymmetrically disposed relative to the cassette in the area adjacent the spring loaded latch 14. As shown in FIGS. 4a, the sensor 30 is a reed switch 30' positioned on the pump, and the actuating element 31' on the cassette is a magnet. In FIG. 4b the sensor 30 is an optical sensor 30" with an interrupter flag 31" on the cassette, and in FIG. 4c the sensor is a mechanical switch 30'" triggered by juxtaposition with finger 31'" protruding from the cassette.

In FIG. 5, the pump is provided with an additional latching pin 13c adjacent to the spring loaded latch 14 and pin 13b. The cassette is notched with a notch 40 in latching element 12b into which pin 13c is fitted. The thickness of element 12b is reduced by notch 40, such that it is just sufficient to fit between latching pins 13b and 13c. Element 12c of the cassette remains too thick for insertion between pins 13b and 13c and the cassette cannot be operatively reversed in orientation. If element 12c were to be similarly notched to avoid the one way keying in this embodiment, it would however be detrimental to system operation since it also causes a loose fit between pins 13a and thus improper pump operation.

FIG. 6 depicts the electronics 50 within pump 1 which contains a microcomputer 51 with memory 52 for determination and comparison of current from current sensor 53 to a stored current range used by the pump with a properly inserted cassette. If the current is too low (compared to the range in memory 52), the microcomputer determines that there is no cassette and pump operation is shut off by cut-off of current to the pump.

It is understood that the above description and drawings are merely illustrative of the present invention and that changes may be made to the structure and the type of sensing components, without departing from the scope of the present invention as defined in the following claims.

What is claimed is:

1. A fluid pumping system comprising a peristaltic fluid dispensing rotary pump having a plurality of rotating rollers and a keyed one way insertable cassette for the peristaltic fluid dispensing rotary pump, with said cassette having compressible tubing adapted to be compressed by the pump, wherein the cassette holds and maintains the compressible tube adjacent rollers of the pump, whereby the rollers of the pump compress the tubing to draw and accurately dispense predetermined exact amounts of liquids from a dispensing container with which the tubing is operatively connected, wherein improper placement of the cassette relative to the pump may result in inaccurate fluid dispensing, characterized in that one of the cassette and pump comprises sensing means which provides an interlock for pump operation and the other of the cassette and pump comprises actuating means for actuating the sensor to permit pump operation and wherein the actuating means actuates the sensing means only when the cassette is in proper operative position relative to the pump, wherein the pump comprises the sensing means and the cassette comprises the pump actuating means, wherein the sensing means comprises means for sensing the presence of the cassette and the sensor actuating means comprising the cassette when properly placed, said sensing means being operable by comparing a predetermined range of current normally used by the pump under load, stored in memory means, when the cassette is properly operatively positioned; to current actually being used by the pump, with pump operation continuing only with sensed current at least that of stored current range.

2. The system of claim 1, wherein a portion of the cassette adapted to be engaged with the pump is keyed to only permit proper engagement of the cassette with the pump.

3. The system of claim 2, wherein said portion of the cassette comprises an area of reduced size relative to another portion of the cassette adapted to be engaged with the pump and the pump comprises a reception area of reduced size adapted to engage and hold only said reduced size portion of the cassette.

\* \* \* \* \*